United States Patent [19]

Yoshioka et al.

[11] Patent Number: 4,970,336
[45] Date of Patent: Nov. 13, 1990

[54] METHOD OF PURIFYING ALPHA-SUBSTITUTED ACETIC ACIDS

[75] Inventors: Yoshikazu Yoshioka; Isao Hashiba; Suketoshi Tsukamoto, all of Onoda, Japan

[73] Assignee: Nissan Chemical Industries, Ltd., Tokyo, Japan

[21] Appl. No.: 359,682

[22] Filed: May 31, 1989

[30] Foreign Application Priority Data

May 31, 1988 [JP] Japan .................. 63-133192

[51] Int. Cl.$^5$ .................................. C07C 59/76
[52] U.S. Cl. ..................... 562/460; 562/426; 562/427; 562/466; 562/478; 562/490; 562/492; 562/494; 562/485
[58] Field of Search ............ 562/485, 494, 460, 490, 562/494, 492, 478, 466, 426, 427

[56] References Cited

U.S. PATENT DOCUMENTS

| | | | |
|---|---|---|---|
| 3,873,613 | 3/1975 | Knobloch | 562/485 |
| 4,201,870 | 5/1980 | Zupancic | 562/460 |
| 4,709,089 | 11/1987 | Shimuzu | 562/494 |

FOREIGN PATENT DOCUMENTS 695028  9/1964  Canada .

*Primary Examiner*—Paul J. Killos
*Attorney, Agent, or Firm*—Oliff & Berridge

[57] ABSTRACT

This invention relates to methods of preparing and purifying α-substituted acetic acids, which comprise treating an α-aromatic-substituted acetic acid represented by a specific general formula with a weak alkali while shielding light, or subjecting an α-aromatic-substituted acetonitrile represented by a specific general formula to acid hydrolysis, followed by treatment with a weak alkali while shielding light; and treating the alkali salt of α-substituted acetic acid thus formed with a decolorizing agent.

19 Claims, No Drawings

METHOD OF PURIFYING ALPHA-SUBSTITUTED ACETIC ACIDS

BACKGROUND OF THE INVENTION

1. Field of the Invention

This invention relates to a method of purifying α-substituted acetic acids.

The α-substituted acetic acids obtained by the method of this invention, such as 2-(3-benzoylphenyl)-propionic acid, have valuable pharmacological properties and are particularly useful as anti-inflammatory drugs.

2. Description of the Prior Art

Japanese Pat. Publication No.8301 (1977) discloses a process for producing 2 (3-benzoylphenyl)alkanoic acids, which comprises hydrolyzing a 2-(3-benzoylphenyl)alkanonitrile by heating it under reflux in an aqueous methanol containing sodium hydroxide, concentrating the reaction mixture, washing the concentrate with diethyl ether, acidifying the aqueous layer with hydrochloric acid, and collecting the product which separated out by filtration, followed by washing with distilled water and drying.

U.S. Pat. No.4,201,870 discloses a process for producing 2-(3-benzoylphenyl)alkanoic acids, which comprises hydrolyzing a 2-(3-benzoylphenyl)alkanonitrile by heating it under reflux in an aqueous methanol containing potassium hydroxide, concentrating the reaction mixture, washing the concentrate with diethyl ether, decolorizing the aqueous layer with activated charcoal, filtering off the activated charcoal, acidifying the filtrate with hydrochloric acid, extracting the product which separated out with diethyl ether, distilling off the ether from the extract, dissolving the residue in acetonitrile, and decolorizing the solution with activated charcoal, followed by crystallization, filtration and drying.

Japanese Pat. Kokai No.115452 (1976) discloses a process for producing 2-(3 benzoylphenyl)alkanoic acids, which comprises hydrolyzing a 2-(3-benzoylphenyl)alkanonitrile by heating it under reflux in an aqueous ethanol containing sodium hydroxide, concentrating the reaction mixture, washing the concentrate with dichloromethane, acidifying the aqueous layer with hydrochlcric acid, extracting the product which separated out with dichloromethane, distilling off the dichloromethane from the extract, and dissolving the residue in diethyl ether, followed by crystallization, filtration and drying.

These conventional methods, in which α-substituted acetic acids are purified in the form of salts with strong alkalis in the light, have the problems that the final products contain colored impurities occasionally assuming dark brown or black color and that their yield is not satisfactory.

In addition, the purification operations are cumbersome and take a long time.

SUMMARY OF THE INVENTION

An object of this invention is to provide a method of purifying α-substituted acetic acids with a high yield in a short time by simple operations.

Another object of this invention is to provide a method of preparing high-purity α-substituted acetic acids from the corresponding α-substituted acetonitriles with a high yield in a short time.

The methods of this invention for preparing and purifying fying α-substituted acetic acids comprise treating an α-aromatic-substituted acetic acid represented by a specific general formula with a weak alkali while shielding light, or subjecting an α-aromatic-substituted acetonitrile represented by a specific general formula to acid hydrolysis, followed by treatment with a weak alkali while shielding light; and treating the alkali salt of α-substituted acetic acid thus obtained with a decolorizing agent.

DETAILED DESCRIPTION OF THE INVENTION

Comprehensive studies on the preparation and purification of α-substituted acetic acids have led us to find that decolorization of these compounds, which was very difficult with conventional methods, can be easily achieved, if an α-substituted acetic acid is treated with a weak alkali while shielding light, or an α-substituted acetonitrile is subjected to acid hydrolysis, followed by treatment with a weak alkali while shielding ligtt, and the alkali salt of α-substituted acetic acid thus obtained is decolorized with a decolorizing agent. High-purity α-substituted acetic acids can thus be obtained with a high yield in a short time by simple operations. This invention was accomplished on the basis of these findings.

Thus, this invention relates to a method of purifying α-substituted acetic acids, which comprises treating an α-substituted acetic acid selected from the compounds represented by the following general formulas [I], [II], [III], [IV]and [V],

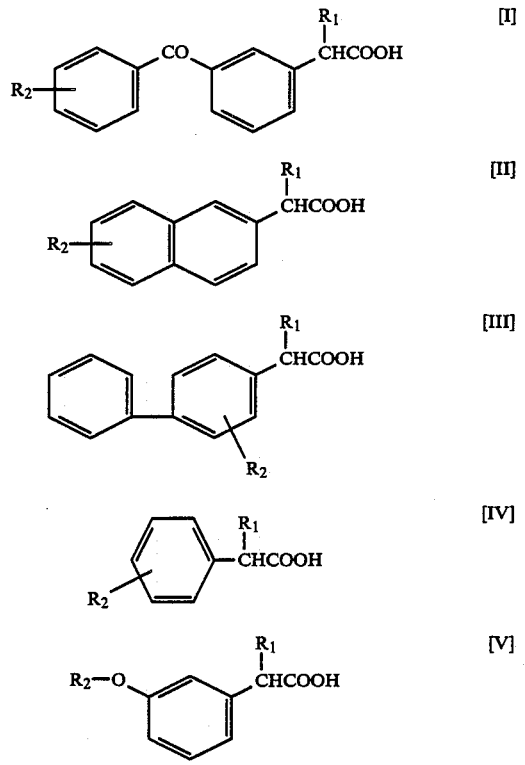

(wherein $R_1$ denotes hydrogen atom, a halogen atom or an alkyl group having 1 to 5 carbon atoms; and $R_2$ stands for hydrogen atom, a halogen atom, an alkoxy group having 1 to 5 carbon atoms, an alkylthio group having 1 to 5 carbon atoms, trifluoromethyl, or an aromatic radical comprising one or more benzene rings)

with a weak alkali selected from alkali bicarbonates, ammonia and magnesium hydroxide while shielding light; and decolorizing the alkali α-substituted acetate thus formed with a decolorizing agent.

This invention also relates to a method of purifying α-substituted acetic acids, which comprises subjecting an α-substituted acetonitrile selected from the compounds represented by the following general formulas [VI], [VII], [VIII], [IX] and [X],

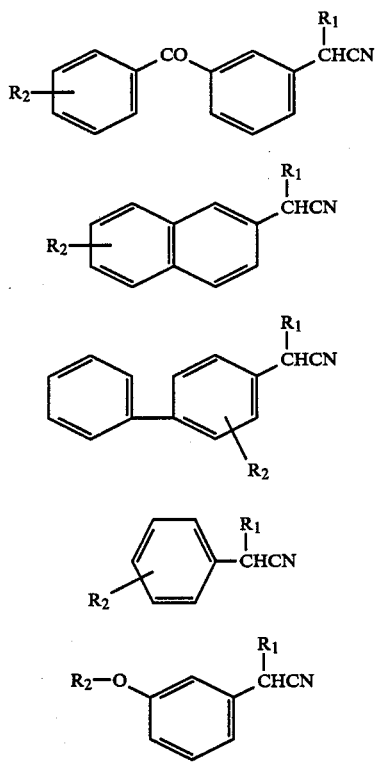

to acid hydrolysis while shielding light; treating the corresponding α-substituted acetic acid thus formed with a weak alkali selected from alkali bicarbonates, ammonia and magnesium hydroxide while shielding light; and decolorizing the alkali α-substituted acetate thus formed with a decolorizing agent.

As examples of $R_1$ in the above formulas, there may be mentioned hydrogen atom; halogen atoms, such as fluorine, chlorine, bromine and iodine; and alkyl groups having 1 to 5 carbon atoms, such as methyl, ethyl, n-propyl, isopropyl, n-butyl, isobutyl, tert-butyl, n-pentyl and isopentyl.

As examples of $R_2$, there may be mentioned hydrogen atom; halogen atoms such as fluorine, chlorine, bromine and iodine; alkoxy groups having 1 to 5 carbon atoms, such as methoxy, ethoxy, n-propoxy, isopropoxy, n-butoxy, isobutoxy, tert-butoxy, n-pentoxy and isopentoxy; alkylthio groups having 1 to 5 carbon atoms, such as methylthio, ethylthio, n-propylthio, isopropylthio, n-butylthio, isobutylthio, tert-butylthio, n-pentylthio and isopentylthio groups; trifluoromethyl group; and aromatic radicals comprising one or more benzene rings, such as phenyl, diphenyl and naphthyl radicals.

As examples of the weak alkalis, may be mentioned alkali bicarbonates, such as sodium bicarbonate, potassium bicarbonate, calcium bicarbonate, magnesium bicarbonate and ammonium bicarbonate; ammonia, such as gaseous ammonia, liquid ammonia and ammonia water; and magnesium hydroxide.

The weak alkali is used in an amount of 1 to 3 mole equivalents, preferably 1.1 to 1.5 mole equivalents, based on the mole of the α-substituted acetic acid selected from the compounds represented by the general formulas [I], [II], [III], [IV] and [V].

The α-substituted acetic acid is treated with the weak alkali at a temperature in the range from 0° C. to 100° C., preferably from 20° C. to 50° C.

As the decolorizing agent, may be used activated charcoal, activated clay or others.

The decolorizing agent is used in an amount of 0.01 to 0.5 part by weight, preferably 0.03 to 0.1 part by weight, based on 1 part by weight of the α-substituted acetic acid.

Decolorization is carried out at a temperature in the range from 20° C. to 100° C., preferably 40° C. to 60° C., over a period of 0.5 to 5 hours, preferably 1 to 2 hours.

As examples of the acid to be used for hydrolysis of the α-substituted acetonitrile selected from the compounds represented by the general formulas [VI], [VII], [VIII], [IX] and [X], may be mentioned hydrochloric and sulfuric acids.

The acid is used in an amount of 2 to 10 mole equivalents, preferably 3 to 5 mole equivalents, based on the mole of the α-substituted acetonitrile.

Acid hydrolysis is carried out at a temperature in the range from 50° C. to 200° C., preferably from 100 to 153° C., over a period of 0.5 to 10 hours, preferably 1 to 5 hours.

In the method of this invention, an inert as is used as required in the steps of acid hydrolysis, salt formation with the weak alkali and decolorization of the alkali salt.

As examples of the inert gas, may be mentioned nitrogen, helium and argon gases.

Described below is a preferred embodiment of this invention.

An α-substituted acetic acid selected from the compounds represented by the general formulas [I], [II], [III], [IV] and [V] is treated with a weak alkali selected from alakli bicarbonates, ammonia and magnesium hydroxide while shielding light, or an α-substituted acetonitrile selected from the compounds represented by the general formulas [VI], [VII], [VIII], [IX] and [X] is subjected to acid hydrolysis while shielding light, followed by treatment with a weak alkali under the same condition; the alkali salt of α-substituted acetic acid thus formed is decolorized with a decolorizing agent; the decolorized solution is acidified with a mineral acid; the free α-substituted acetic acid which separates out is extracted with an organic solvent, such as benzene, toluene, chloroform, diethyl ether, diisopropyl ether and ethyl acetate; and the final product is crystallized out from the extract, collected by filtration and dried.

The acid thus obtained is white crystals, which are dissolved in methanol, giving a colorless and transparent solution.

As may be apparent from the foregoing, use of a weak alkali for neutralization of α-substituted acetic acids in place of strong alkalis, and performing the purification steps (neutralization and acid hydrolysis) while shielding light, gave final products as white crystals (forming a colorless and transparent solution when dissolved in methanol) unlike the products prepared by conventional methods.

The following examples will further illustrate the invention but are not intended to limit its scope.

EXAMPLE 1

A reactor fitted with a stirrer, a thermometer and a condenser was shielded from light, nitrogen gas was introduced therein, and reaction was carried out as described below.

Fifty grams of 60% sulfuric acid was placed in the reactor, 11.8 g 2-(3-benzoylphenyl)propionitrile was added dropwise over a period of 30 minutes while maintaining the temperature at 120° C. to 130° C., and the reaction was continued at 130° C. for four hours.

At the end of reaction, 100 ml toluene and 100 ml water were added to dissolve the reaction product, the mixture was allowed to stand, and the aqueous layer separated was removed.

The toluene layer was washed with water, 100 ml water and 7 g sodium bicarbonate were added, the mixture was stirred well and then allowed to stand, and the toluene layer was removed.

To the aqueous layer was added 1 g activated charcoal, the mixture was stirred at 50° C. for two hours and then allowed to cool to room temperature, the activated charcoal was filtered off, and this decolorization operation was repeated once again.

After adding 10 g of 35% hydrochloric arid to the filtrate, 100 g toluene was further added, the mixture was stirred well and then allowed to stand, and the aqueous layer separated was removed. The toluene layer was washed with water, most of the toluene was distilled off, and the concentrate was allowed to cool. The crystals which separated out were collected by filtration, washed with toluene and dried, giving 9.9 g of 2-(3-benzoylphenyl)propionic acid as white powder ( m.p. 95° C. ).

The methanolic solution of this powder was colorless and transparent, with the UV transmittance at 430 nm being 99%.

The total yield of 2(3- benzoylphenyl) propionic acid reached 95%.

EXAMPLE 2

Reaction was carried out in much the same way as in Example 1 except that nitrogen gas was not used.

The total yield of 2-(3-benzoylphenyl)propionic acid was 96%.

Its methanolic solution was colorless and transparent, with the UV transmittance at 430 nm being 97%.

EXAMPLE 3

A reactor fitted with a stirrer, a thermometer and a condenser was shielded from light, nitrogen gas was introduced therein, and reaction was carried out as described below.

To a solution of 2 g 2-(3-benzoylphenyl)propionic acid ( a product which, when dissolved in methanol, gives a yellow-colored transparent solution showing UV transmittance at 430 nm of 90% ) in 10 ml toluene, were added 30 ml water and 2 g sodium bicarbonate, the mixture was stirred well and then allowed to stand, and the toluene layer separated was removed.

To the aqueous layer was added 0.2 g activated charcoal, the mixture was stirred at 50° C. for two hours and then allowed to cool to room temperature, the activated charcoal was filtered off, and this decolorizatior operation was repeated once again.

After adding 3.5 g of 35% hydrochloric acid to the filtrate, 50 ml toluene was further added, the mixture was stirred well and then allowed to stand, and the aqueous layer separated was removed. The toluene layer was washed with water, most of the toluene was distilled off, and the concentrate was allowed to cool. The crystals which separated out were collected by filtration, washed with toluene and dried, giving 1.6 g of 2-(3-benzoylphenyl)propionic acid as white powder ( m.p. 95° C.).

The methanolic solution of this powder was colorless and transparent, with the UV transmittance at 430 nm being 99%.

EXAMPLE 4

Reaction was carried out in much the same way as in Example 3 except that nitrogen gas was not used.

2-(3-Benzoylphenyl)propionic acid ( m.p. 95° C. ) was obtained as white powder. The yield was was 1.6 g ( 80% ).

Its methanolic solution was colorless and transparent, with the UV transmittance at 430 nm being 98%.

EXAMPLE 5

A reactor fitted with a stirrer, a thermometer and a condenser was shielded from light, nitrogen gas was introduced therein, and reaction was carried out as described below.

Fifty grams of 60% sulfuric acid was placed in the reactor, 11.8 g 2-(3-benzoylphenyl)propionitrile was added dropwise over a period of 30 minutes while maintaining the temperature at 120° to 130° C., and the reaction was continued at 130° C. for four hours.

At the end of reaction, 100 ml toluene and 100 ml water were added to dissolve the reaction product, the mixture was stirred well and then allowed to stand, and the aqueous layer separated was removed.

The toluene layer was washed with water, 100 ml water and 5 g of 28% ammonia water were added, the mixture was stirred well and then allowed to stand, and the toluene layer separated was removed.

The aqueous layer was treated in the same way as in Example 1, giving 11.8 g of 2-(3-benzoylphenyl)propionic acid as white powder ( m.p. 95° C. ).

The methanolic solution of this powder was colorless and transparent, with the UV transmittance at 430 nm being 99%.

The total yield of the product was 93%.

REFERENCE EXAMPLE 1

A reactor fitted with a stirrer, a thermometer and a condenser was shielded from light, nitrogen gas was introduced therein, and reaction was carried out as described below.

Fifty grams of 60% sulfuric acid was placed in the reactor, 11.8 g 2-(3-benzoylphenyl)propionitrile was slowly added dropwise while maintaining the temperature at 120° C. to 130° C., and the reaction was continued at 130° C. for four hours.

At the end of reaction, 100 ml toluene and 100 ml water were added to dissolve the reaction product, the mixture was stirred well and then allowed to stand, and the aqueous layer separated was removed.

The toluene layer was washed with water, 100 g of 3.3% aqueous solution of sodium hydroxide was added, the mixture was stirred well and then allowed to stand, and the toluene layer separated was removed.

The aqueous layer was treated in the same way as in Example 1, giving 12.1 g of 2-(3-benzoylphenyl)propionic acid as yellow powder (m.p. 95° C.).

When dissolved in methanol, it gave a yellow-colored transparent solution showing UV transmittance at 430 nm of 95%.

The total yield of the product was 95%.

REFERNCE EXAMPLE 2

Nitrogen gas was introduced into a reactor fitted with a stirrer, a thermometer and a condenser without being shielded from light, and reaction was carried out as described below.

A mixture of 11.8 g 2-(3-benzoylphenyl)propionitrile and 100 g of 50% aqueous methanol containing 2.5 g sodium hydroxide was placed in the reactor and heated under reflux for 24 hours.

The reaction mixture was concentrated at 50° C. under a reduced pressure of 20 mmHg, 100 ml water was added to the concentrate, the mixture was stirred well, and the resulting solution was washed twice with 100 ml diethyl ether.

To the aqueous layer was added 10 g of 35% hydrochloric acid, and the crystals which separated out were collected by filtration, washed with water and dried, giving 7.6 g of 2-(3-benzoylphenyl)propionic acid as brown solid (m.p. 93° C.).

When dissolved in methanol, it gave a brown-colored transparent solution showing UV transmittance at 430 nm of 90%.

The total yied of the product was 60%.

REFERENCE EXAMPLE 3

Nitrogen gas was introduced into a reactor fitted with a stirrer, a thermometer and a condenser without being shielded from light, and reaction was carried out as described below.

A mixture of 11.8 g 2-(3-benzoylphenyl)propionitrile and 100 g of 50% aqueous methanol containing 3.4 g potassium hydroxide was placed in the reactor and heated under reflux for 24 hours.

The reaction mixture was concentrated under reduced pressure, 100 ml water was added to the concentrate, the mixture was stirred well, and the resulting solution was washed twice with 100 ml diethyl ether.

To the aqueous layer was added 1 g activated charcoal, the mixture was stirred at 50° C. for two hours and then allowed to cool to room temperature, and the activated charcoal was filtered off.

Ten grams of 35% hydrochloric acid was added to the filtrate, 100 ml diethyl ether was further added, the mixture was stirred well and then allowed to stand, and the aqueous layer separated was removed.

After distilling off the diethyl ether, the residue was dissolved in 100 ml toluene, 1 g activated charcoal was added to the solution, and the mixture was stirred at 50° C. for two hours.

After cooling to room temperature, the activated charcoal was filtered off, the filtrate was cooled to −15° C. and the crystals which separated out were collected by filtration, washed with diethyl ether and dried, giving 7.0 g of 2-(3-benzoylphenyl)propionic acid as white powder (m.p. 95° C.).

When dissolved in methanol, it gave a colorless and transparent solution showing UV transmittance at 430 nm of 95%.

The total yield of the product was 55%.

What is claimed is:

1. A method of purifying α-substituted acetic acid, which comprises treating an α-substituted acetic acid with a weak alkali selected from alkali bicarbonates, ammonia and magnesium hydroxide while shielding light, the α-substituted acetic acid being selected from the compounds represented by the following formulas I, II, III, IV and V:

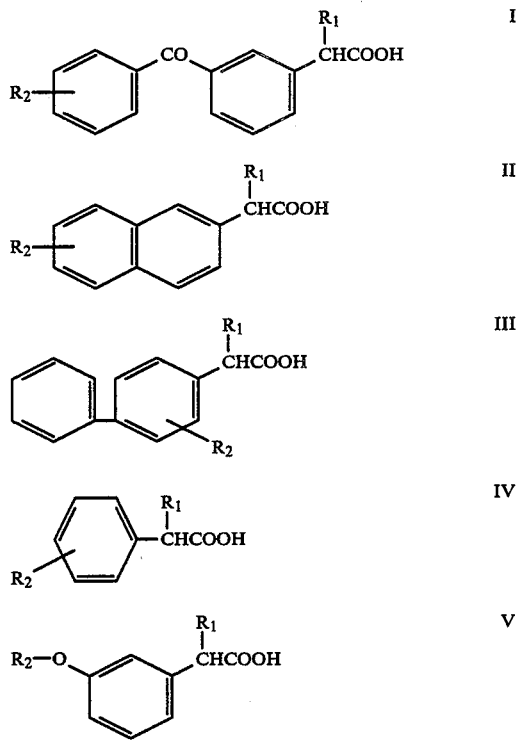

wherein $R_1$ denotes a hydrogen atom, a halogen atom or an alkyl group having 1 to 5 carbon atoms; and $R_2$ denotes a hydrogen atom, a halogen atom, an alkoxy group having 1 to 5 carbon atoms, an alkylthio group having 1 to 5 carbon atoms, a trifluoromethyl, or an aromatic radical comprising one or more benzene rings; and decolorizing the alkali α-substituted acetate thus formed with a decolorizing agent.

2. The method as defined in claim 1, wherein said α-substituted acetic acid is 2-(3-benzoylphenyl) propionic acid.

3. The method as defined in claim 2, wherein said weak alkali is sodium bicarbonate or ammonia water.

4. The method as defined in claim 2, wherein said weak alkali is used in an amount of 1 to 3 mole equivalents based on moles of the α-substituted acetic acid.

5. The method as defined in claim 2, wherein the α-substituted acetic acid is treated with said weak alkali at a temperature in the range of 0° C. to 100° C.

6. The method as defined in claim 2, wherein said decolorizing agent is activated charcoal.

7. The method as defined in claim 2, wherein said decolorizing agent is used in an amount of 0.01 to 0.5 part by weight based on 1 part by weight of the α-substituted acetic acid.

8. The method as defined in claim 2, wherein decolorization is carried out at a temperature in the range from 20° C. to 100° C.

9. A method of purifying α-substituted acetic acid, which comprises subjecting an α-substituted acetonitrile to acid hydrolysis while shielding light, the α-substituted acetonitrile being selected from the compounds represented by the folowing formulas VI, VII, VIII, IX and X:

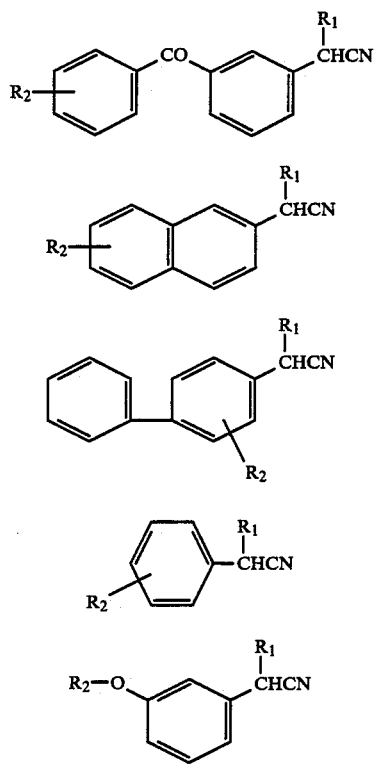

wherein $R_1$ denotes a hydrogen atom, a halogen atom or an alkyl group having 1 to 5 carbon atoms; and $R_2$ denotes a hydrogen atom, a halogen atom, an alkoxy group having 1 to 5 carbon atoms, an alkylthio group having 1 to 5 carbon atoms, a trifluoromethyl, or an aromatic radical comprising one or more benzene rings; treating the α-substituted acetic acid thus formed with a weak alkali selected from alkali bicarbonates, ammonia and magnesium hydroxide while shielding light; and treating the alkali α-substituted acetate thus formed with a decolorizing agent.

10. The method as defined in claim 9, wherein said α-substituted acetonitrile is 2-(3-benzoylphenyl) propionitrile and the α-substituted acetic acid produced is 2-(3-benzoyl-phenyl) propionic acid.

11. The method as defined in claim 10, wherein sulfuric acid is used for the acid hydrolysis.

12. The method as defined in claim 10, wherein the acid hydrolysis is carried out by the use of sulfuric acid in an amount of 2 to 10 mole equivalents based on moles of the α-substituted acetonitrile.

13. The method as defined in claim 10, wherein the acid hydrolysis is carried out at a temperature in the range from 50° C. to 200° C.

14. The method as defined in claim 10, wherein said weak alkali is sodium bicarbonate or ammonia water.

15. The method as defined in claim 10, wherein said weak alkali is used in an amount of 1 to 3 mole equivalents based on moles of the α-substituted acetic acid formed.

16. the method as defined in claim 10, wherein the α-substituted acetic acid formed is treated with said weak alkali at a temperature in the range from 0° C. to 100° C.

17. The method as defined in claim 10, wherein said decolorizing agent is activated charcoal.

18. The method as defined in claim 10, wherein said decolorizing agent is used in an amount of 0.01 to 0.5 part by weight based on 1 part by weight of the α-substituted acetic acid formed.

19. The method as defined in claim 10, wherein decolorization is carried out at a temperature in the range from 20° C. to 100° C.

* * * * *